United States Patent [19]
Flohr

[11] Patent Number: 5,701,360
[45] Date of Patent: Dec. 23, 1997

[54] FOURIER RECONSTRUCTION OF COMPUTER TOMOGRAPHY IMAGES WHICH REPRESENT A SELECTABLE REGION OF THE EXAMINATION SUBJECT

[75] Inventor: Thomas Flohr, Uehlfeld, Germany

[73] Assignee: Siemens Aktiengesellschaft, Munich, Germany

[21] Appl. No.: 533,334

[22] Filed: Sep. 25, 1995

Related U.S. Application Data

[63] Continuation-in-part of Ser. No. 226,335, Apr. 12, 1994, abandoned.

[30] Foreign Application Priority Data

May 7, 1993 [DE] Germany ............... 43 15 279.1

[51] Int. Cl.$^6$ ................................................ G06K 9/00
[52] U.S. Cl. .............. 382/131; 382/132; 364/413.15; 364/413.2; 378/4
[58] Field of Search ............... 382/131, 132, 382/128; 364/413.13, 413.14, 413.15, 413.16, 413.18, 413.19, 413.2, 413.21; 378/4, 901

[56] References Cited

U.S. PATENT DOCUMENTS

| | | |
|---|---|---|
| 4,257,102 | 3/1981 | Horiba et al. ............... 364/414 |
| 4,562,540 | 12/1985 | Devaney ............... 364/400 |
| 4,616,318 | 10/1986 | Crawford ............... 364/414 |
| 4,891,829 | 1/1990 | Deckman et al. ............... 378/4 |
| 4,991,093 | 2/1991 | Roberge et al. ............... 364/413.15 |
| 5,128,864 | 7/1992 | Waggener et al. ............... 364/413.21 |
| 5,293,312 | 3/1994 | Waggener ............... 364/413.21 |
| 5,307,264 | 4/1994 | Waggener et al. ............... 364/413.21 |
| 5,384,573 | 1/1995 | Turpin ............... 342/179 |

OTHER PUBLICATIONS

"A Holographic Coordinate Transform Based System for Direct Fourier Tomographic Reconstruction", Huang et al., SPIE vol. 1564, Optical Information Processing Systems and Architectures III (1991), pp. 664–665.

"The Mathematics of Computerized Tomography,", Natterer (1966), pp. 102–108.

Primary Examiner—Leo Boudreau
Assistant Examiner—Bipin Shawala
Attorney, Agent, or Firm—Hill, Steadman & Simpson

[57] ABSTRACT

A computer tomography apparatus, wherein data obtained from radiation penetrating an examination subject are present in parallel beam geometry, undertakes a Fourier reconstruction of computer tomography images which represent a selectable region of the examination subject. The reconstruction is undertaken by extending and modifying a known gridding techniqud for Fourier reconstruction of computer tomography images. Values on a rectangular grid with grid dimension η in the frequency domain are obtained by weighting the values on the polar grid with a function $\hat{G}$. The grid dimension η in the frequency space may be arbitrarily chosen for generating an excerpt $|x-x_0|\leq L=\frac{1}{2}\eta$ and $|y-y_0|\leq L=\frac{1}{2}\eta$ of the examination volume. The spectral values on the rectangular grid are periodically repeated in Cartesian Coordinates with a period length M/L, wherein L is the sidelength of the image field and M·M is the number of picture elements, resulting in a plurality of contributions falling into the basic period. A two-dimensional Fourier transform of the spectrum in Cartesian Coordinates back to the spatial domain is applied to the basic period to produce the image.

1 Claim, 5 Drawing Sheets

Small Field of view L·L
center at $\vec{r}_0 = (r_0 \cos \vartheta_0, r_0 \sin \vartheta_0)$
$= (x_0, y_0)$

FOURIER RECONSTRUCTION OF COMPUTER TOMOGRAPHY IMAGES WHICH REPRESENT A SELECTABLE REGION OF THE EXAMINATION SUBJECT

RELATED APPLICATION

The present application is a continuation-in-part of application Ser. No. 08/226,335, filed Apr. 12, 1994, and now abandoned.

BACKGROUND OF THE INVENTION

1. Field of the Invention

The present invention is directed to a computer tomography apparatus, an in particular to a computer tomography apparatus of the type wherein data are supplied by the radiation detector in parallel beam geometry to a computer which calculates the tomogram from the data.

2. Description of the Prior Art

Computer tomography systems are known in the art wherein an examination subject is irradiated by penetrating x-rays, with the attenuated radiation being incident on a radiation detector, and wherein the computer to which the data are supplied calculates a tomogram therefrom, using one of numerous image reconstruction algorithms.

If the data are supplied from the radiation detector to the computer in a format corresponding to parallel beam geometry, a problem exists in the art to reconstruct the tomographic image in a manner which permits the representation of an arbitrarily selectable region of the examination subject in the image. U.S. Pat. No. 4,257,102, for example, discloses the representation of an arbitrarily selectable region of the subject by means of a convolution rear projection reconstruction. This technique requires calculations to be undertaken which are relatively complicated and time consuming.

SUMMARY OF THE INVENTION

It is an object of the present invention to provide a computer tomography apparatus wherein data are supplied by the radiation detector in parallel beam geometry to a computer for calculating a tomographic image of the examination subject, wherein an arbitrarily selectable region of the subject can be represented in the tomographic image.

The above object is achieved in accordance with the principles of the present invention in a computer tomography system wherein a Fourier reconstruction is employed for generating the tomographic image. As used herein, a Fourier reconstruction of the tomographic image means the generation of an image from line integrals. This is to be distinguished from reprojection techniques such as the generation of line integrals in a known image.

In general, the computer tomography apparatus constructed in accordance with the principles of the present invention employs a known gridding technique which results in values arising at the grid intersections, which are each multiplied in accordance with the invention by a phase factor which takes the position of the current point in the local space into consideration. An arbitrary excerpt of the gridded image can then be defined dependent on the Cartesian grid dimension in the frequency space. The periodic repetition of the spectrum in Cartesian coordinates with a mathematically defined period length is also taken into account, and all contributions within the selected region are then summed. A two-dimensional Fourier transformation of the values generated in this manner is then undertaken.

DESCRIPTION OF THE PREFERRED EMBODIMENTS

Figure 1:
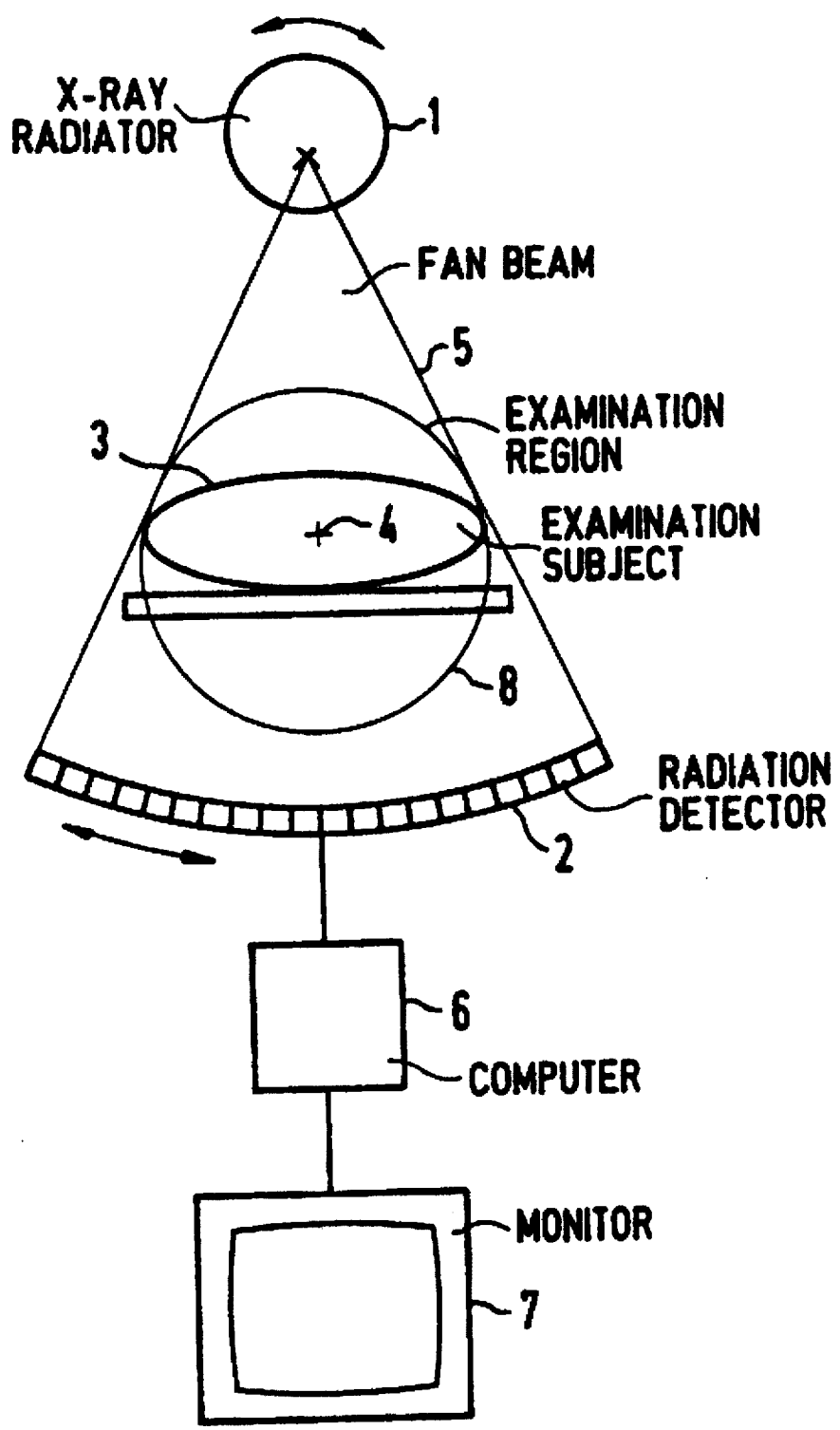
FIG. 1 shows a computer tomography apparatus constructed and operating in accordance with the principles of the present invention.
Figure 2:
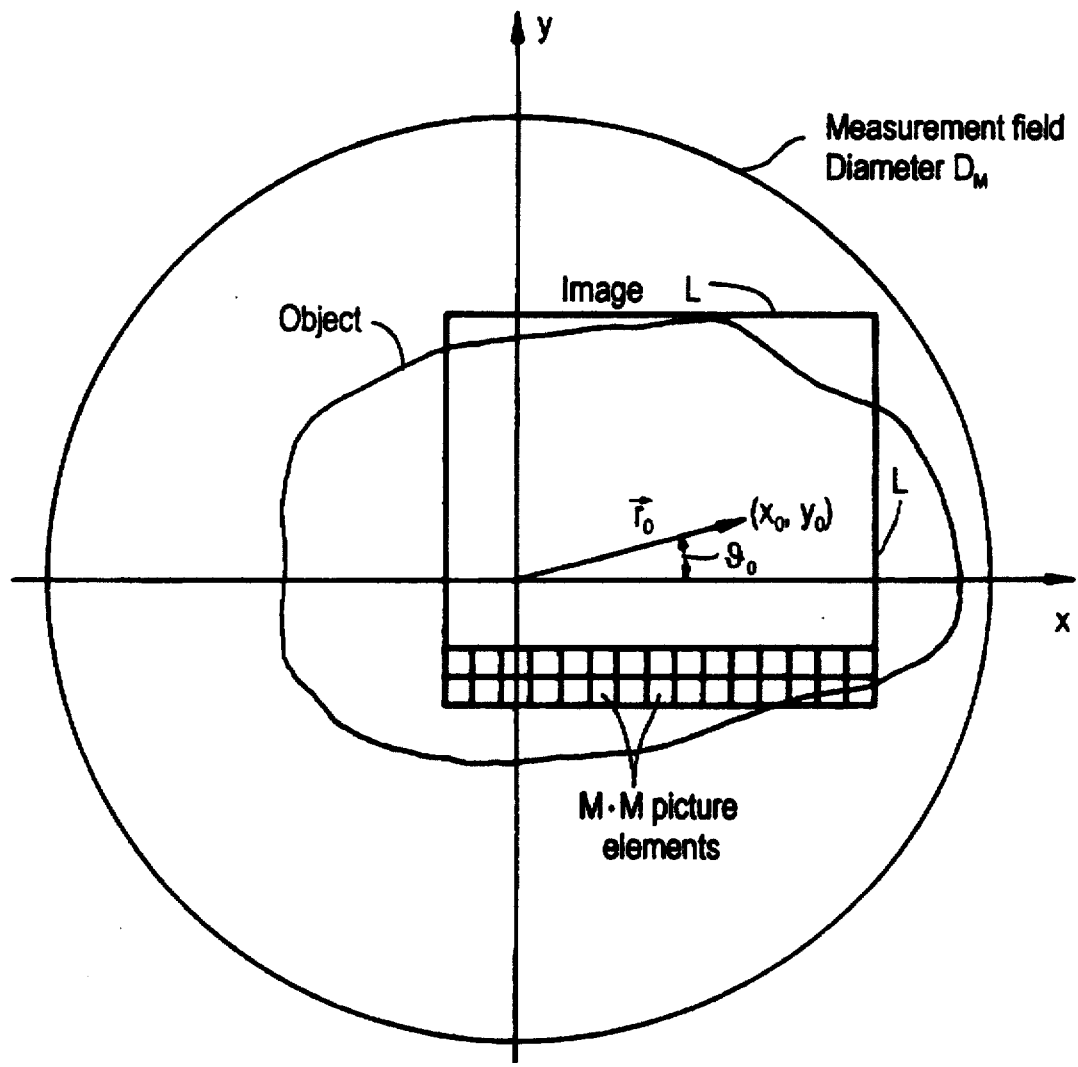
FIG. 2 shows an image with M×M elements and the sidelength L×L in the spatial domain.
Figure 3:
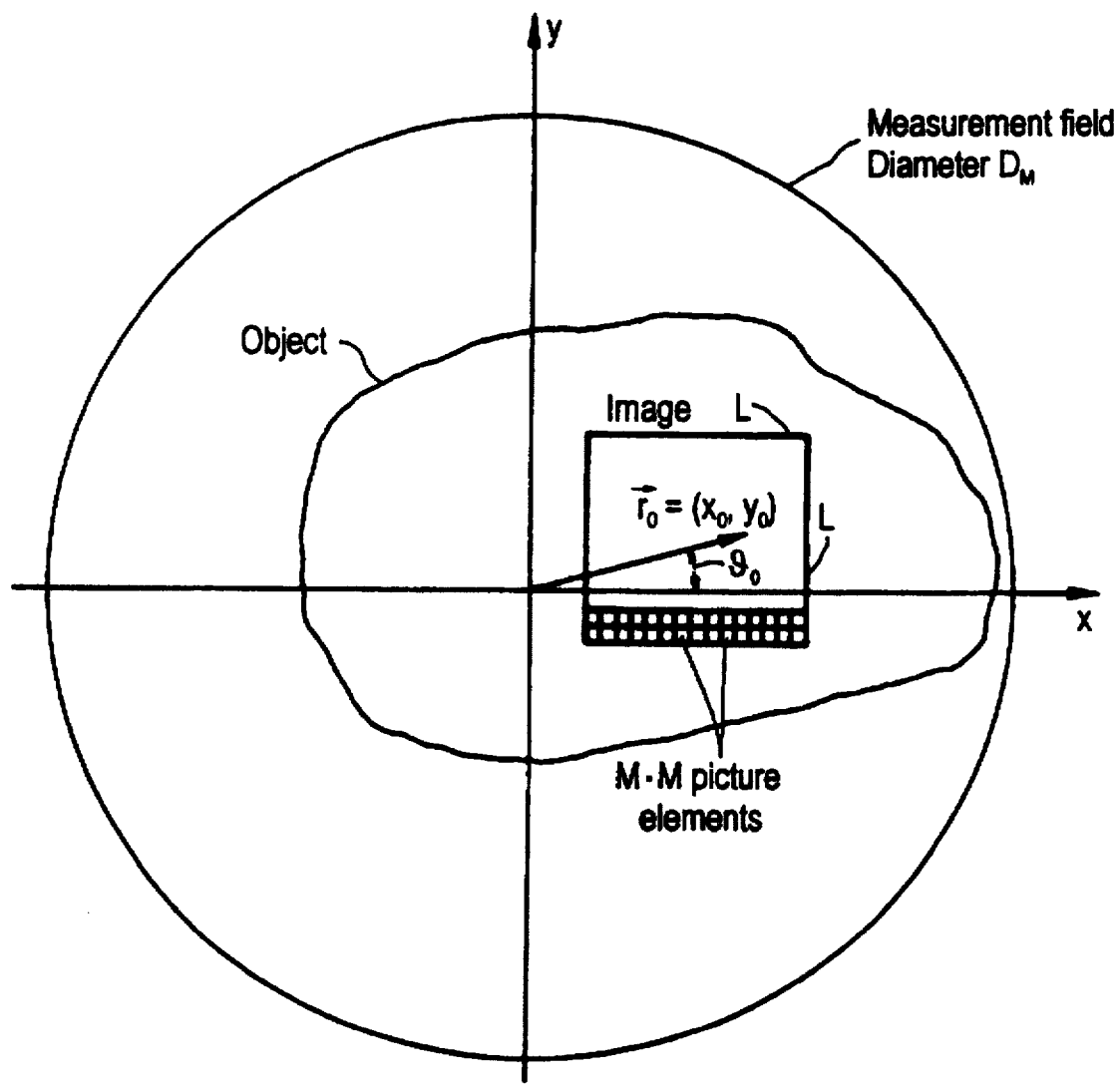
FIG. 3 corresponds to FIG. 2 with a small field of view and the same number of picture elements M×M for the small field of view and for the large field of view according to FIG. 2. M may be chosen arbitrarily.
Figure 4:
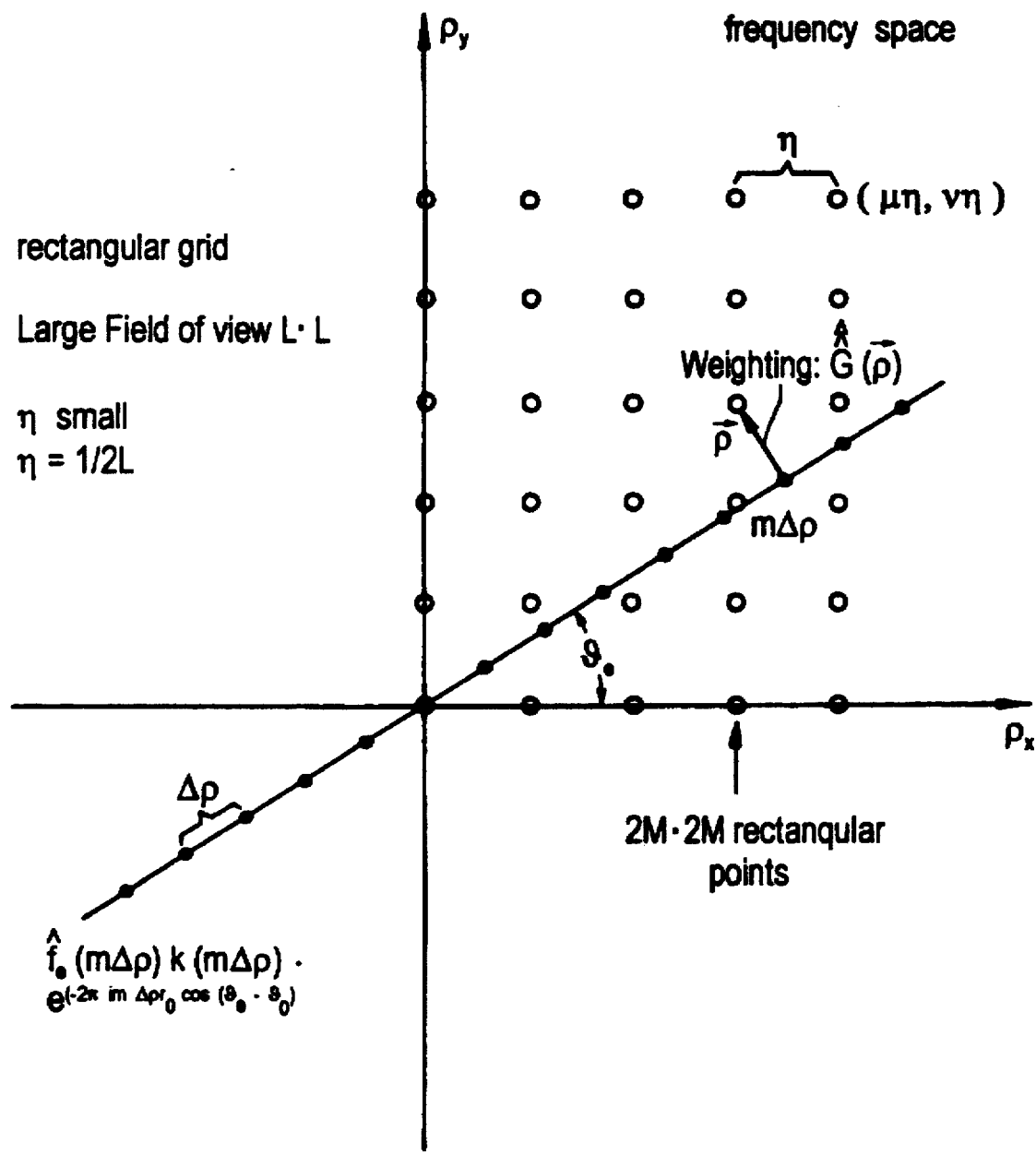
FIG. 4 shows a rectangular grid, in the frequency space, which is transformed back to the spatial domain according to FIG. 1.
Figure 5:
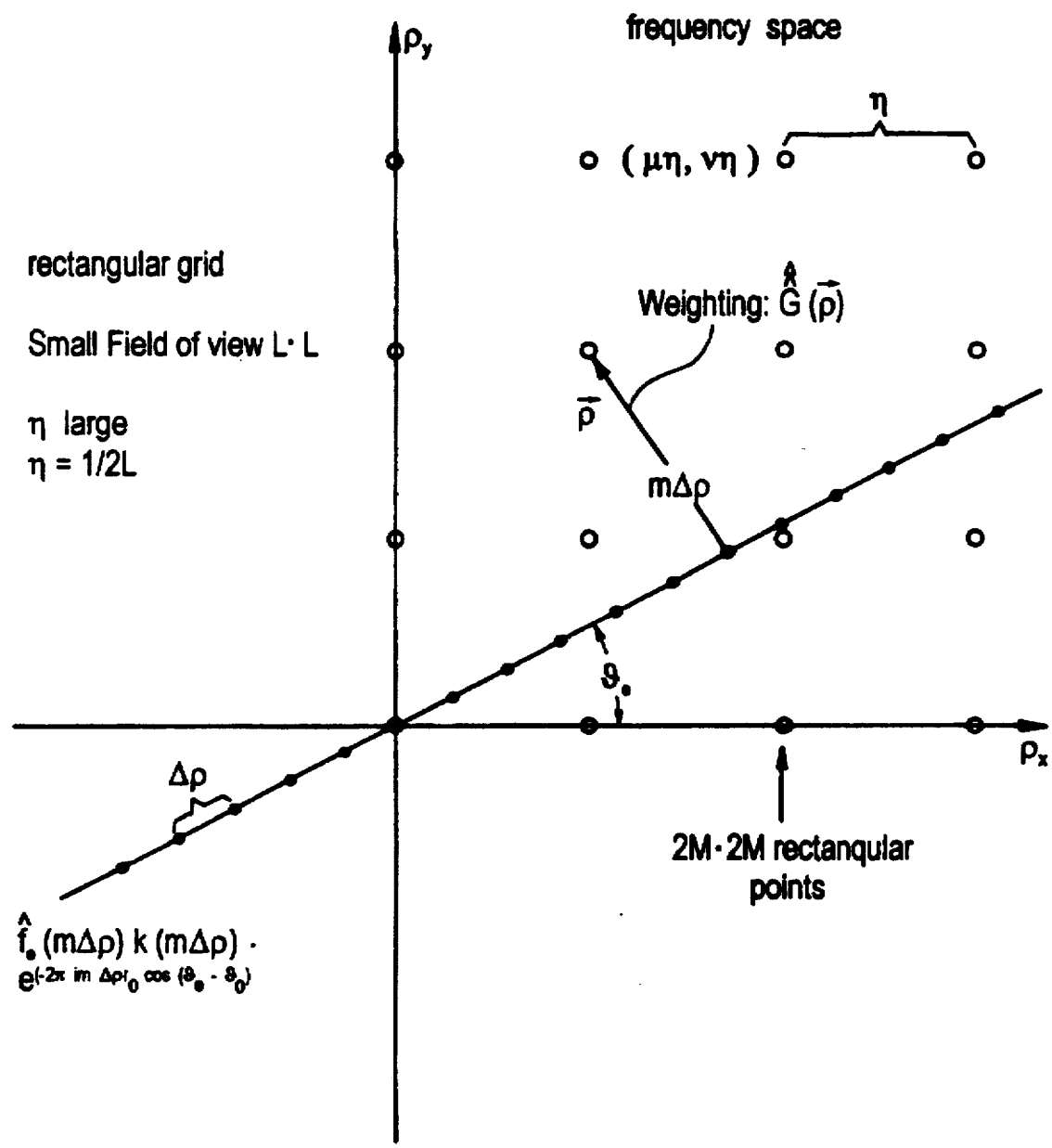
FIG. 5 shows a rectangular grid in the frequency space, which is transformed back to the spatial domain according to FIG. 2.

A computer tomography apparatus constructed in accordance with the principles of the present invention includes an x-ray radiator 1 and a radiation detector 2 composed of a series of detector elements. The x-ray radiator 1 and the radiation detector 2 are rotated around a system axis 4 for scanning a subject 3, so that the subject 3 is irradiated from various directions by a fan-shaped x-ray beam 5 emanating from the x-ray radiator 1. The detector elements respectively generate output signals corresponding to the radiation incident thereon, which are supplied in parallel beam geometry format to a computer 6, which reconstructs a tomogram of the subject 3 for display on a monitor 7. The subject 3 is disposed in a measuring field 8 which is irradiated by the x-ray beam 5.

For the purpose of explaining the image reconstruction which takes place in the computer 6 in accordance with the principles of the present invention, let a discrete CT parallel data set $f_{lk}$ of a scan subject located in the measuring field 8 (diameter $D_M$) be given. The parallel data set is characterized in that the data $f_{lk}$ are present in a plane perpendicular to the rotational axis of the CT apparatus, and belong to discrete directions $\vec{n}_l = (\cos \dot{v}_l, \sin \dot{v}_l)$, with $\dot{v}_l = (l-1)\pi/N_p$, wherein l designates the projection under consideration and $N_p$ is the projection number. Let the scan grid in the direction of $\vec{n}_l$ be "a", so that $P_{k+1} - P_k = a$ is valid for the scan points $P_k$ in the direction of $\vec{n}_l$. The parallel beam data are either directly measured, or are produced by interpolation of data which were measured with other arrangements, (for example, using fan beam geometry).

The tomographic image of an arbitrary subject region around a point $\vec{r}_0 = (x_0, y_0) = (r_0 \cos \dot{v}_0, r_0 \sin \dot{v}_0)$ is to be produced from the tomographic parallel beam $f_{lk}$ of a scan subject located in the measuring field 8 having the diameter $D_M$, with $|x-x_0| \leq L$ and $|y-y_0| \leq L$. The values L and $\vec{r}_0$ are freely selectable; the number M×M of the illustrated picture elements is not dependent on L, and the limiting sharpness of the reconstruction $\rho_{max}$ is independent of L.

Discrete Fourier transformation of the data $f_{lk}$ of each projection l is undertaken, so that values $\hat{f}_l(m\Delta\rho)$ (meaning $\hat{f}_l$ is a function of $m\Delta\rho$) in the two-dimensional frequency space $\vec{\rho}$ allocated to $\vec{r}$ arise only at the grid points (arc $\rho)_l = \dot{v}_l$ and $|\vec{\rho}_m| = m\Delta\rho$ with $\Delta\rho \leq \tfrac{1}{2}N_a = \tfrac{1}{2}D_M$ and m∈z of a polar grid. $\Delta\rho$ is the sampling distance on the polar grid in the radial direction. Multiplication of these values by a function $K(m\Delta\rho)$, which influences the image sharpness, is then undertaken.

Reconstruction is accomplished by combining a known gridding method with the multiplication of the values $\hat{f}_l$ $(m\Delta\rho)$ $K(m\Delta\rho)$ by a phase factor, variation of the Cartesian grid dimension in the frequency space for generating an arbitrary image excerpt, and taking into account the periodic repetition of the spectrum in Cartesian coordinates.

In detail, the values of the product function $\hat{f}_l$ $(m\Delta\rho)$ $K(m\Delta\rho)$ are multiplied by a phase factor $\exp(-2\pi i \vec{\rho} \cdot \vec{r}_0) = \exp(-2\pi i m\rho_0 \cos(\Delta\upsilon_l - \upsilon_0))$, of the current point in the local space into consideration. The variation of the Cartesian grid dimension $\eta$ in the frequency space is employed for generating an arbitrary image excerpt $|x-x_0| \leq L \sim 1/\eta$, $|y-y_0| \leq L \sim 1/\eta$ of the subject region. The periodic repetition of the spectrum in Cartesian coordinates with a period length M/L (M×M being the number of presented picture elements and L being the edge length of the image field) is employed in the summing of all contributions falling into the basic period, so that the function $K(m\Delta\rho)$ which influences the image sharpness can be selected such that $\hat{f}_l$ $(m\Delta\rho)$ $K(m\Delta\rho)$ $>0$ for $|m\Delta\rho| \geq m/2L$ is valid.

After multiplication of $\hat{f}_l$ $(m\Delta\rho)$ by K $(m\Delta\rho)$, the product is multiplied by $\exp(-2\pi i \vec{\rho} \cdot \vec{r}_0)$ $\exp(-2\pi i \vec{\rho} \cdot \vec{r}_0) = \exp(-2\pi i m\rho_0 \cos(\Delta\upsilon_l - \upsilon_0)) = 0$.

A gridding technique is undertaken, such as by generating a rectangular grid having the grid point coordinates $$\rho_{x\mu} = \mu\eta \text{ and } \rho_{y\upsilon} = \upsilon\eta \text{ with } \eta < \tfrac{1}{2}L \text{ and } \mu, \upsilon \in Z,$$

from the values in the polar grid points by addition of contributions which arise by the multiplication of the values in the polar grid points by a weighting function $\hat{G}(\vec{\rho})$, which is dependent on the distance of the rectangular grid point under consideration from the polar grid points. The weighting function $\hat{G}(\vec{\rho})$ is of such a nature that its Fourier transform $G(\vec{r})$ in the local space falls as steeply as possible in a region $|\vec{r}|>L$ below a prescribed value (for example $10^{-4}$). The value $\eta$ is variable and controls the size of the selected image excerpt to be displayed.

The spectrum $\hat{B}(\mu\eta, \upsilon\eta)$ which arose as a result of the above gridding is periodically repeated with a period length M/L in the $\rho_x$ and $\rho_y$ directions, whereby M×M is the number of displayed picture elements in the local space, and L is the edge length of the image field. The spectrum $\hat{B}(\mu\eta, \upsilon\eta)$ is centered around the coordinate origin. The addition of all contributions is then undertaken which arise due to the periodic repetition of the spectrum $\hat{B}(\mu\eta, \upsilon\eta)$.

A two-dimensional discrete Fourier transformation of the values generated using the basic period of $\hat{B}(\mu\eta, \upsilon\eta)$ is undertaken in rectangular grid points, and multiplication of the resulting numerical values which are now present in the local space by a normalization function $1/G(r)$ is undertaken. The picture elements lying in the preselected region $|x-x_0| \leq L$ and $|y-y_0| \leq L$ represent the desired image.

As a supplement to the above basic operation of the computer tomography apparatus of the invention, one or more of the following variants can be practiced. The data $f_{lk}$ of each projection 1 can be directly convolved with K(r) in the local space, clipping the values at $|\rho|=D_M/2$, followed by a one-dimensional Fourier transformation of the obtained values with $\Delta\rho' \leq 1/N_a = 1/D_M$.

Discrete Fourier transformation of the data $f_{lk}$ for each projection 1 can be undertaken, so that values $\hat{f}_l(m\Delta\rho)$ arise in the two-dimensional frequency space $\vec{\rho}$ allocated to $\vec{r}$ at the grid points of a polar grid $\upsilon_l$, and $\rho_m = m\Delta\rho$ with $\Delta\rho \leq \tfrac{1}{2}N_a = \tfrac{1}{2}D_M$. These values are then multiplied by $K(m\Delta\rho)$, followed by an inverse transformation of the resulting values $\hat{f}_l(m\Delta\rho) K(m\Delta\rho)$ in the local space. These values are limited or clipped at $|\rho|=D_M/2$. A renewed, discrete Fourier transformation is then undertaken such that values at the grid points of a polar grid (arc $\rho)_l = \upsilon_l$ and $\rho_\eta = \eta\Delta\rho'$, with $\Delta\rho'=1/D_M$ arise in the frequency space.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising:

means for irradiating an examination subject disposed in an examination volume from different directions with penetrating radiation;

means for detecting said penetrating radiation from said different directions attenuated by said subject and for generating electrical signals corresponding to the attenuated radiation comprising a data set in parallel beam geometry; and computer means for constructing an image of an arbitrary excerpt of the overall examination volume by Fourier reconstruction, including means for one-dimensional Fourier transform of the input data in parallel geometry $f_{lk} = f(\rho_k, \upsilon_l)$ with respect to $\rho_k$, resulting in values $\hat{f}_l$ $(m\Delta\rho)$ on a polar grid $|\vec{\rho}_m|=m\Delta\rho$ and arc $\vec{\rho}=\upsilon_l$ in the frequency domain, means for multiplying the product $\hat{f}_l$ $(m\Delta\rho)$ $K(m\Delta\rho)$ by a phase factor $\exp(-2\pi i \vec{\rho} \cdot \vec{r}_0) = \exp(-2\pi i m\Delta\rho r_0 \cos (\upsilon_l - \upsilon_0))$, wherein $\vec{r}_0 = (r_0 \cos \upsilon_0, r_0 \sin \upsilon_0) = (x_0, y_0)$ is the position of the center point of the desired image field in the spatial domain, means for calculating values on a rectangular grid with grid dimension $\eta$ in the frequency domain by weighting the values on the polar grid with a function G, whereby the grid dimension $\eta$ in the frequency space may be arbitrarily chosen for generating an excerpt $|x-x_0| \leq L = \tfrac{1}{2}\eta$ and $|y-y_0| \leq L = \tfrac{1}{2}\eta$ of said examination volume, means for periodically repeating said spectral values on the rectangular grid in Cartesian Coordinates with a period length M/L, wherein L is the sidelength of the image field and M·M is the number of picture elements, resulting in a plurality of contributions falling into the basic period, means for summing said plurality of contributions in the basic period for selecting the function $K(m\Delta\rho)$ such that $\hat{f}_l$ $(m\Delta\rho)$ $K(m\Delta\rho) \geq 0$ for $|m\Delta\rho| \geq M/2L$ is valid, and means for two-dimensional Fourier transform of the basic period of the spectrum in Cartesian Coordinates back to the spatial domain to produce the image.

\* \* \* \* \*